(12) United States Patent
Mahadevan-Jansen et al.

(10) Patent No.: US 8,300,220 B2
(45) Date of Patent: Oct. 30, 2012

(54) DEVICE AND METHOD FOR NON-INVASIVELY EVALUATING A TARGET OF INTEREST OF A LIVING SUBJECT

(75) Inventors: Anita M. Mahadevan-Jansen, Nashville, TN (US); David Dickensheets, Bozeman, MT (US); Chad Lieber, Nashville, TN (US)

(73) Assignees: Vanderbilt University, Nashville, TN (US); Montana State University, Bozeman, MT (US)

( * ) Notice: Subject to any disclaimer, the term of this patent is extended or adjusted under 35 U.S.C. 154(b) by 360 days.

(21) Appl. No.: 12/713,071

(22) Filed: Feb. 25, 2010

(65) Prior Publication Data

US 2010/0214562 A1 Aug. 26, 2010

Related U.S. Application Data

(60) Provisional application No. 61/155,404, filed on Feb. 25, 2009.

(51) Int. Cl.
*G01J 3/44* (2006.01)
(52) U.S. Cl. ............................. 356/301; 356/73; 600/473
(58) Field of Classification Search .................... 356/73, 356/301, 479; 600/473, 476
See application file for complete search history.

(56) References Cited

U.S. PATENT DOCUMENTS

| | | | |
|---|---|---|---|
| 7,508,524 B2* | 3/2009 | Mahadevan-Jansen et al. | 356/479 |
| 7,542,132 B2* | 6/2009 | Fang et al. | 356/72 |
| 7,972,107 B2* | 7/2011 | Dervaux et al. | 415/115 |
| 2004/0046121 A1* | 3/2004 | Golden et al. | 250/339.07 |

OTHER PUBLICATIONS

R. Richards-Kortum et al., Quantitative optical spectroscopy for tissue diagnosis, Annu. Rev. Phys. Chem., 1996, p. 555-606, vol. 47.
N. Ramanujam, Fluorescence spectroscopy of neoplastic and non-neoplastic tissues, Neoplasia, 2000, p. 89-117, vol. 2, Cancer Facts and Figures, American Cancer Society.
A. Mahadevan-Jansen et al., Raman Spectroscopy for the Detection of Cancers and Precancers, J. of Biomed Optics, Jan. 1996, p. 31-70, vol. 1, No. 1.
A. Robichaux Viehoever et al., Organotypic raft cultures as an effective in vitro tool for understanding Raman spectral analysis of tissue, Photochemistry and Photobiology, 2003, p. 517-524, vol. 78, No. 5.

* cited by examiner

*Primary Examiner* — Layla Lauchman
(74) *Attorney, Agent, or Firm* — Morris Manning & Martin LLP; Tim Tingkang Xia, Esq.

(57) ABSTRACT

A probe using integrated confocal reflectance imaging, confocal Raman spectroscopy, and gross spatial imaging for non-invasively evaluating a target of interest of a living subject. In one embodiment, the probe includes a casing with first and second ends, and first, second and third optical pons The firsi and second optical ports are located at the first end of the casing and the third optical port is located at the second end of the casing such that the first and third optical ports define a first optical path therebetween and the second and third optical ports define a second optical path therebetween, respectively. Each optical path has first and second portions, where the second portions of the first and second optical paths arc substantially overlapped and proximal to the third optical port.

25 Claims, 4 Drawing Sheets

DEVICE AND METHOD FOR NON-INVASIVELY EVALUATING A TARGET OF INTEREST OF A LIVING SUBJECT

CROSS-REFERENCE TO RELATED PATENT APPLICATION

This application claims the benefit, pursuant to 35 U.S.C. §119(e), of provisional U.S. Patent Application Ser. No. 61/155,404, filed Feb. 25, 2009, entitled "DEVICE AND METHOD FOR NON-INVASIVELY EVALUATING A TARGET OF INTEREST OF A LIVING SUBJECT", by Anita Mahadevan-Jansen, David Dickensheets, and Chad Lieber, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [4] represents the 4$^{th}$ reference cited in the reference list, namely, A. Viehoever Robichaux, D. Anderson, E. D. Jansen, A. Mahadevan-Jansen, "Organotypic raft cultures as an effective in vitro tool for understanding Raman spectral analysis of tissue," *Photochemistry and Photobiology*, 78(5), p. 517-524, 2003.

STATEMENT OF FEDERALLY-SPONSORED RESEARCH

This invention was made with Government support under Contract No. NIH/NCI R01CA114471 awarded by the National Institute of Health and National Cancer Institute. The Government has certain rights in the invention.

FIELD OF THE INVENTION

The present invention generally relates to a device and method for non-invasive evaluation of a target of interest of a living subject, and in particular to devices and methods that integrate confocal imaging with confocal Raman spectroscopy, for non-invasive evaluation of the biochemical compositions and morphological details of normal and cancerous skin lesions of a living subject.

BACKGROUND OF THE INVENTION

Optical spectroscopy can provide automated, fast and non-intrusive characterization of normal and non-normal tissues [1,2]. Specifically, Raman spectroscopy, a powerful technique that probes the biochemistry of the tissue, can be used to provide accurate differential diagnosis of early disease [3]. Recent studies indicate the need to isolate the signatures from the different layers of tissue [4]. Confocal Raman spectroscopy provides such characterization with optical sectioning. However, Raman spectroscopy is a purely biochemical technique and yields limited information about the tissue microstructure. Additionally, Raman signals can be too weak for imaging.

Therefore, a heretofore unaddressed need exists in the art to address the aforementioned deficiencies and inadequacies.

SUMMARY OF THE INVENTION

In one aspect, the present invention relates to a probe using integrated confocal reflectance imaging, confocal Raman spectroscopy, and gross spatial imaging for non-invasively evaluating a target of interest of a living subject. In one embodiment, the probe includes a casing with a first end and an opposite, second end. The probe further includes a first optical port, a second optical port, and a third optical port, where the first and second optical ports are located at the first end of the casing and the third optical port is located at the second end of the casing. The first and third optical ports define a first optical path between them and the second and third optical ports define a second optical path between them, respectively, where each of the first and second optical paths has a first portion and a second portion, and where the second portions of the first and second optical paths are substantially overlapped and proximal to the third optical port. The probe also includes a collimation lens, a coupling lens, and an objective lens assembly, as well as a first mirror, a second mirror, and a third mirror. Further, the probe includes a band pass filter, a long pass filter, a scanning member, an electronic imaging device, and a focus control device. The casing of the probe is configured to be a handheld device.

Moreover, the probe is further configured such that the collimation lens, the band pass filter, and the second mirror are placed at the first portion of the first optical path, and the coupling lens, the long pass filter, and the first mirror are placed at the first portion of the second optical path. Also, the second and third mirrors, the scanning member, and the objective assembly are placed at the overlapped second portion of the first and second optical paths.

In one embodiment, the probe in operation has an excitation light that is received from the first optical port and collimated by the collimation lens, then passed through the band pass filter and reflected to the scanning member by the second mirror. The scanning member scans the excitation light through the objective assembly and the third optical port onto the target of interest, which in response, produces backscattered light. The backscattered light includes elastically scattered light and wavelength shifted Raman light, which is collected through the third optical port by the objective assembly. The light collected through the third optical port is then de-scanned and reflected by the scanning member and the third mirror to the second mirror, from which the elastically scattered light is reflected by the second mirror to the band pass filter and transmitted through the band pass filter and the coupling lens to the first optical port. The wavelength shifted Raman light, on the other hand, is reflected by the second mirror to the first mirror, and reflected by the first mirror to the long pass filter, and transmitted through the long pass filter and the coupling lens to the second optical port. In one embodiment, the elastically scattered light includes morphologic information on the target of interest, and the wavelength shifted Raman light includes information on biochemical content of the target of interest. Further, the target of interest of a living subject includes tissue of a living subject. With regard to the excitation light received from the first optical port, it has a wavelength in the range of 600-1000 nanometers. Also, the collimating lens is adapted for collimating the excitation light received from a single mode fiber that is optically coupled with the first optical port, and the coupling lens is adapted for focusing the wavelength shifted Raman light onto a multimode fiber that is optically coupled with the second optical port.

In one embodiment, the objective lens assembly is dynamically engaged with a focusing mechanism for selectively translating the position of the objective lens assembly in relation to the target of interest, for controlling depth of focus on the target of interest. The second mirror is a dichroic mirror configured to selectively transmit the wavelength shifted Raman light and to reflect away light that is not the wavelength shifted Raman light. The third mirror is a hot mirror adapted for selectively transmitting the visible light for use by the electronic imaging device and reflecting away non-visible light. In this embodiment, the scanning member is a bi-axial MEMS mirror adapted for raster-scanning a beam of the excitation light onto the target of interest. The electronic imaging device is a CCD camera optically coupled to both the third mirror and the scanning member, and it is adapted for receiving the visible light transmitted by the hot mirror and capturing at least one real-time image of a selected area of the target of interest from the received visible light. This captured image(s) is a low resolution bright-field image containing gross spatial information on the morphology of the selected area of the target of interest. The probe further has an optically transparent window that is placed at the second end of the casing between the third port and a position where the target of interest is to be placed, in operation, and the window has a ring LED adapted for providing bright-field illumination to the target of interest.

In another aspect, the present invention relates to a method of non-invasively evaluating a target of interest of a living subject, using a handheld integrated probe for confocal reflectance imaging, confocal Raman spectroscopy, and gross spatial imaging. In one embodiment, the method includes the steps of capturing at least one gross spatial image of a selected area of the target of interest. Based on the at least one captured gross spatial image, at least one confocal image is selectively captured, which corresponds to a first specific area within the selected area of the target of interest. Based on the at least one captured confocal image, Raman spectra is selectively captured which corresponds to a second specific area within the first specific area of the target of interest. The captured confocal image(s) and captured Raman spectra corresponding to the target of interest are then compared with corresponding known signatures for at least one known condition for a target area of interest. In one embodiment, the target of interest of the living subject is skin tissue and the condition is a skin disease. In another embodiment, the skin disease is a skin cancer.

Moreover, in one embodiment, the gross spatial image(s) is a real-time bright-field image, the confocal image(s) contains information on the morphology of the first specific area, and the Raman spectra contain information on the biochemistry corresponding to the second specific area.

In yet another aspect, the present invention relates to a method for diagnosing skin cancer in a living subject. In one embodiment, the method includes the steps of providing an integrated probe for confocal reflectance imaging, confocal Raman spectroscopy, and gross spatial imaging, and the step of using the integrated probe. The step of using the probe includes performing the steps of capturing at least one gross spatial image of a selected area of the skin containing a target of interest. Based on the at least one captured gross spatial image, at least one confocal image is then captured, which corresponds to a first specific area of the lesion of interest, within the selected area of the skin. Additionally, based on the at least one captured confocal image, Raman spectra are captured which correspond to a specific site of interest within the first specific area of the lesion of interest. In one embodiment, the method also includes the steps of comparing the captured at least one confocal image and captured Raman spectra corresponding to the selected area of skin, with known corresponding signatures for normal skin tissue and malignant skin tissue. In this embodiment, the casing of the probe is configured to be a handheld device.

In yet another aspect, the present invention relates to an optical probe for non-invasively evaluating a target of interest of a living subject. In one embodiment, the probe includes a casing with a first end and an opposite, second end. The casing of the probe is configured to be a handheld device. The probe further includes a first optical port, a second optical port, and a third optical port, where the first and second optical ports are located at the first end of the casing and the third optical port is located at the second end of the casing. The first and third optical ports define a first optical path between them and the second and third optical ports define a second optical path between them, respectively, where each of the first and second optical paths has a first portion and a second portion, and where the second portions of the first and second optical paths are substantially overlapped and proximal to the third optical port. The probe also includes a collimation lens, a coupling lens, and an objective lens assembly, as well as a first mirror, a second mirror, and a third mirror. Further, the probe includes a band pass filter, a long pass filter, a scanning member, an electronic imaging device, and a focus control device.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
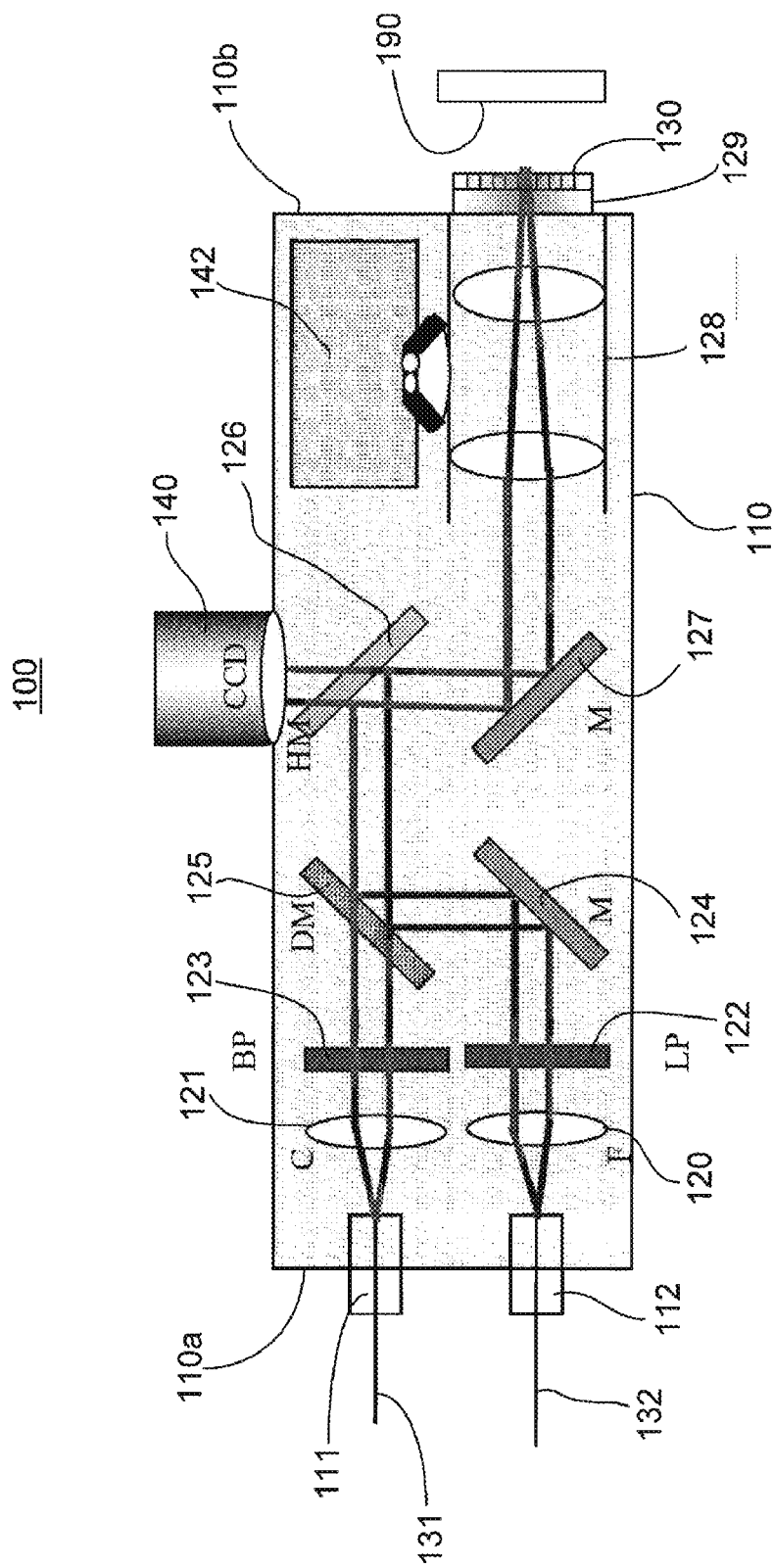
FIG. 1 shows schematically a confocal Raman probe for non-invasively evaluating a target of interest of a living subject.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

OVERVIEW OF THE INVENTION

The American Cancer Society recommends that the best way to find skin cancers early is to recognize changes in existing skin lesions or the appearance of new lesions by regular self-examination. One way to facilitate this routine examination of skin lesions would be the availability of an easy-to-use, non-invasive device that scanned the body in a relatively short time. Such a device could be utilized through the general physician's office or the dermatologist's office to track any suspicious lesions over time.

Skin cancer detection relies on histology followed by simple or layered excision, depending on the type and extent of the pathology found. Regular visual inspection and pre-emptive removal of suspicious lesions is standard in the management of this disease. However, if a tool could be developed that objectively provided definitive diagnosis of a lesion and simplified tracking of skin lesions over time, routine non-essential removal of unsure lesions could be avoided and patient care could be more efficiently managed. In patients who do not undergo routine examination of skin lesions, such a tool would be even more essential. The diagnostic method would have to be effective in differentiating normal skin tissue from benign lesions, such as nevi, from malignant lesions, in a real-time, effective manner that would otherwise be hard to identify accurately using current techniques.

As detailed below, these needs are addressed by the present invention.

The description will be made as to the embodiments of the present invention in conjunction with the accompanying drawing FIGS. 1-4. Now referring first to FIG. 3, in one aspect, the present invention relates to a probe 300 using integrated confocal reflectance imaging, confocal Raman spectroscopy, and gross spatial imaging for non-invasively evaluating a target of interest 390 of a living subject. In one embodiment as shown, the probe 300 includes a casing 310 with a first end 310*a* and an opposite, second end 310*b*. The probe 300 further includes a first optical port 311, a second optical port 312, and a third optical port 313, where the first and second optical ports 311, 312 are located at the first end 310*a* of the casing 310 and the third optical port 313 is located at the second end 310*b* of the casing 310, respectively. The first and third optical ports 311, 313 define a first optical path 315 between them, and the second and third optical ports 312, 313 define a second optical path 316 between them, respectively, where each of the first and second optical paths 315, 316 has a first portion 315*a*, 316*a* and a second portion 315*b*, 316*b*, and where the second portions 315*b*, 316*b* of the first and second optical paths 315, 316 are substantially overlapped and proximal to the third optical port 313. The probe 300 also includes a collimation lens 321, a coupling lens 320, and an objective lens assembly 328, as well as a first mirror 324, a second mirror 325, and a third mirror 326. Further, the probe 300 includes a band pass filter 323, a long pass filter 322, a scanning member 327, an electronic imaging device 340, and a focus control device 342. The casing 310 of the probe 300 is configured to be a handheld device.

Moreover, the probe 300 is further configured such that the collimation lens 321, the band pass filter 323, and the second mirror 325 are placed at the first portion 315*a* of the first optical path 315, and the coupling lens 320, the long pass filter 322, and the first mirror 324 are placed at the first portion 316*a* of the second optical path 316. Also, the third mirror 326, the scanning member 327, and the objective assembly 328 are placed at the overlapped second portion 315*b*, 316*b* of the first and second optical paths 315, 316.

In one embodiment, the probe 300 in operation has an excitation light that is received from the first optical port 311 and collimated by the collimation lens 321, then passes through the band pass filter 323 before being reflected to the scanning member 327 by the second mirror 325. The scanning member 327 scans the excitation light through the objective assembly 328 and the third optical port 313 onto the target of interest 390, which in response, produces backscattered light, including elastically scattered light and wavelength shifted Raman light. The backscattered light is collected through the third optical port 313 by the objective assembly 328. The light collected through the third optical port 313 is then de-scanned and reflected by the scanning member 327 and the third mirror 326 to the second mirror 325, from which the elastically scattered light is reflected by the second mirror 325 to the band pass filter 323 and transmitted through the band pass filter 323 and the coupling lens 321 to the first optical port 311. The wavelength shifted Raman light, on the other hand, is reflected by the second mirror 325 to the first mirror 324, and reflected by the first mirror 324 to the long pass filter 322, and transmitted through the long pass filter 322 and the coupling lens 320 to the second optical port 312. In one embodiment, the elastically scattered light includes morphologic information on the target of interest 390 and the wavelength shifted Raman light includes information on biochemical content of the target of interest 390, respectively. Further, the target of interest of a living subject 390 includes tissue or tissues of a living subject. The excitation light received from the first optical port 311 has a wavelength in the range of 600-1000 nanometers and is delivered from a single mode fiber 331 to the first optical port 311, which is optically coupled to the single mode fiber 331. Also, the collimating lens 321 is adapted for collimating the excitation light received from the first optical port 311, and the coupling lens 320 is adapted for focusing the wavelength shifted Raman light onto a multimode fiber 332 that is optically coupled with the second optical port 312.

In one embodiment, the objective lens assembly 328 is dynamically engaged with a focusing mechanism 342 for selectively translating the position of the objective lens assembly 328 in relation to the target of interest 390, for controlling depth of focus on the target of interest 390. The second mirror 325 is a dichroic mirror configured to selectively transmit the wavelength shifted Raman light and to reflect away light that is not the wavelength shifted Raman light. The third mirror 326 is a hot mirror adapted for selectively transmitting the visible light for use by the electronic imaging device 340 and reflecting away non-visible light. In this embodiment, moreover, the scanning member 327 is a bi-axial MEMS mirror adapted for raster-scanning a beam of the excitation light onto the target of interest 390. The electronic imaging device 340 can be a CCD camera optically coupled to both the third mirror 326 and the scanning member 327, and adapted for receiving the visible light transmitted by the hot mirror 326 and capturing at least one real-time image of a selected area of the target of interest 390 from the received visible light. This captured image(s) is a low resolution bright-field image containing gross spatial information on the morphology of the selected area of the target of interest 390, which also can be seen in FIG. 4. The probe 300 further has an optically transparent window 329 that is placed at the second end 310b of the casing 310 between the third port 313 and a position where the target of interest 390 is to be placed, in operation, and the window has a ring LED 330 adapted for providing bright-field illumination to the target of interest 340.

In another aspect, the present invention relates to a method of non-invasively evaluating a target of interest of a living subject, using a handheld integrated probe 300 for confocal reflectance imaging, confocal Raman spectroscopy, and gross spatial imaging. Now referring to FIG. 4, in one embodiment, the method 400 includes the steps of capturing at least one gross spatial image 492 of a selected area of the target of interest 490. Based on the at least one captured gross spatial image 492, at least one confocal image 494 is selectively captured, which corresponds to a first specific area within the selected area of the target of interest 490. Based on the at least one captured confocal image 494, Raman spectra 496 is selectively captured which corresponds to a second specific area within the first specific area of the target of interest 390. The captured confocal image(s) 494 and captured Raman spectra 496 corresponding to the target of interest 490 are then compared with known corresponding signatures for at least one known condition for a target area of interest 490. In one embodiment, the target of interest of the living subject is skin tissue and the condition is a skin disease. In another embodiment, the skin disease is a skin cancer. Moreover, in one embodiment, the gross spatial image(s) 492 is a real-time bright-field image, the confocal image(s) contains information on the morphology of the first specific area, and the Raman spectra 496 contain information on the biochemistry corresponding to the second specific area.

In yet another aspect, the present invention relates to a method for diagnosing skin cancer in a living subject. In one embodiment, the method includes the steps of providing an integrated probe 300 for confocal reflectance imaging, confocal Raman spectroscopy, and gross spatial imaging, and the step of using the integrated probe 300. The step of using the probe 300 includes performing the steps of capturing at least one gross spatial image 492 of a selected area of the skin containing a target of interest. Based on the at least one captured gross spatial image 492, at least one confocal image 494 is then captured, which corresponds to a first specific area of the lesion of interest, within the selected area of the skin. Additionally, based on the at least one captured confocal image 494, Raman spectra 496 are captured which correspond to a specific site of interest within the first specific area of the lesion of interest. In one embodiment, the method also includes the steps of comparing the captured at least one confocal image 494 and captured Raman spectra 496 corresponding to the selected area of skin, with known corresponding signatures for normal skin tissue and malignant skin tissue. In this embodiment, the casing 310 of the probe 300 is configured to be a handheld device.

In yet another aspect, the present invention relates to an optical probe 300 for non-invasively evaluating a target of interest 390 of a living subject. In one embodiment, the probe 300 includes a casing 310 with a first end 310a and an opposite, second end 310b. The casing 310 of the probe 300 is configured to be a handheld device. The probe 300 further includes a first optical port 311, a second optical port 312, and a third optical port 313, where the first and second optical ports 311, 312 are located at the first end of the casing 310a and the third optical port 313 is located at the second end of the casing 310b. The first and third optical ports 311, 313 define a first optical path 315 between them, and the second and third optical ports 312, 313 define a second optical path 316 between them, respectively, where each of the first and second optical paths 315, 316 has a first portion 315a, 316a and a second portion 315b, 316b, and where the second portions 315b, 316b of the first and second optical paths 315, 316 are substantially overlapped and proximal to the third optical port 313. The probe 300 also includes a collimation lens 321, a coupling lens 320, and an objective lens assembly 328, as well as a first mirror 324, a second mirror 325, and a third mirror 326. Further, the probe 300 includes a band pass filter 323, a long pass filter 322, a scanning member 327, an electronic imaging device 340, and a focus control device 342.

These and other aspects of the present invention will become apparent from the following description of the preferred embodiment taken in conjunction with the drawings, although variations and modifications therein may be affected without departing from the spirit and scope of the novel concepts of the disclosure.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

This example relates to a clinical, confocal Raman instrument, according to one embodiment of the present invention, with confocal imaging as well as bright-field imaging capability for the differential diagnosis of skin lesions by providing real-time, automated, non-intrusive spectral as well as spatial information about the tissue biochemistry as well as structure.

A compact handheld Raman probe with video imaging capability is first described, in connection with FIG. 1 of the drawings. Next, a handheld confocal imaging device at video rate is described, in connection with FIG. 2 of the drawings. An integrated handheld confocal Raman/scanning confocal imaging handheld device according to one exemplary embodiment of the present invention is then described in connection with FIGS. 3 and 4.

Now referring to FIG. 1, the dimensions of the probe 100 are determined by the microscope objective being used and the other commercially available mounts that are used for the optics. A custom objective is designed such that the probe dimensions with all the optics will be roughly 5×5×10 cm and about 150 g in weight. As shown, the objective lens is mounted on a roller bearing slide with piezoelectric drive 142 (Micro Pulse Systems, CA) to provide focus control and have 0.35 NA similar to the existing probe. With a reduced back aperture into the objective, ¼" optics will be used and flexure optical mounts will be built into the chassis thus eliminating the excess space occupied by the current commercial mounts. Additionally, video imaging will be added to guide the region for Raman sampling (see e.g. CCD camera 140). A ring light LED 130 will be mounted around the probe window 129 for bright-field illumination. The Raman illumination beam will be visible in the video field of view, allowing for image guidance of Raman sampling from regions of interest. A color CCD chip 140 is attached to the probe head 110 to capture a video image of a region of skin (~5×5 mm²), on a target of interest 190. A hot mirror 126 in the beam path separates the visible light from the Raman signal. A dichroic mirror 125 separates the collected Raman light from the excitation source, which is further cleaned using a long pass filter 122 in the beam path. The resultant light is focused onto a 100 μm multimode fiber 132, which forms the confocal aperture for the Raman signal. The spatial resolution of the probe 100 is about 7 μm laterally and 20 μm axially.

The probe 100 is connected via an "umbilical chord" to the illumination and collection system (through optical fibers 131, 132). A TE-cooled CCD camera 140 is used, since a fiber coupled ECDL used as an illumination source may get overheated and as a result have a tendency to mode hop over prolonged use. Overheating can be avoided by separating the diode/grating assembly from the electronics of the ECDL, and adding a cooling fan. A reticule is used to minimize any voluntary and involuntary motions of a patient being evaluated, relative to the handpiece. In addition, an aiming beam is incorporated for visual guidance of placement. A single graphical user interface (e.g. using Labview or Windows programming) is also used, with the ability to display video images, grab frames, highlight a region for Raman acquisition and acquire and display spectra. This simplifies data acquisition and archiving.

Figure 2:
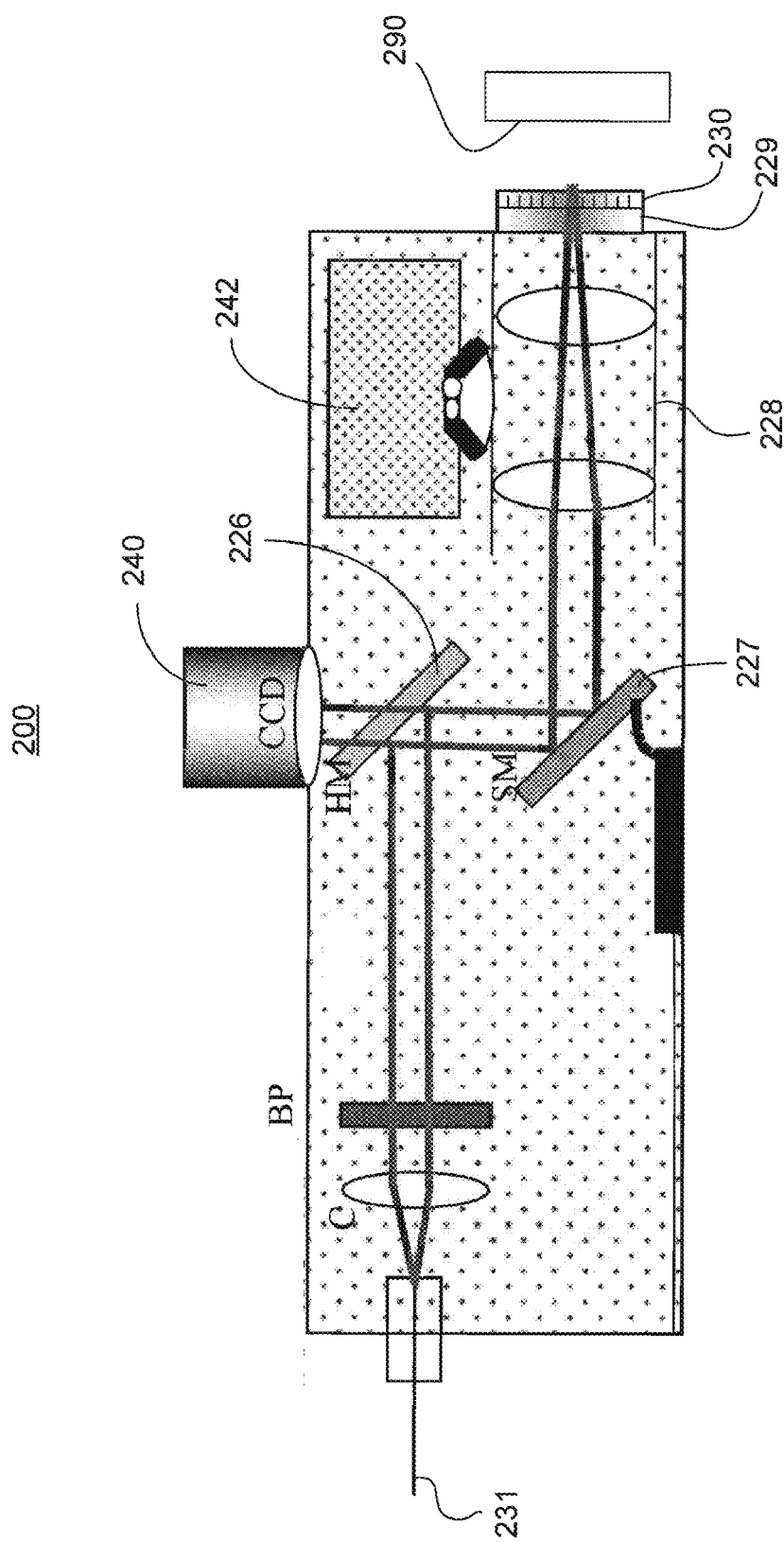
FIG. 2 shows schematically a confocal imaging probe for non-invasively evaluating a target of interest of a living subject.

Now referring to FIG. 2, a handheld confocal imaging device 200 at video rate is described. By incorporating the ability to obtain morphologic images, structural information can be obtained from tissue of a target of interest 290 of a living subject. Histology, the traditional gold standard for cancer diagnosis, relies on structural information in its implementation. Thus, morphologic imaging provides real-time histology. By integrating this imaging modality to confocal Raman spectroscopy, qualitative structural as well as quantitative biochemical information about the tissue state is obtained. The choice of confocal reflectance imaging as the method of obtaining morphology simplifies design of the device. Some advantages of this method are that (a) the same illumination used in confocal Raman measurements may be used for the imaging source, (b) the design may be maintained relatively simple and (c) the expertise as well as the track record in confocal imaging to build such an instrument is available. Thus, the cellular imaging capability of confocal imaging is used to aid in interpreting the Raman signals in the context of local cellular morphology. Not only does the combination of these technologies provide a cellular basis for the Raman data, but also the combination of cellular morphology coupled with the chemical specificity provides a powerful multimodal diagnostic tool. Following a modular design a stand alone confocal imaging probe and device 200 is built for parallel testing of its benefit along side the confocal Raman probe. A central component is a bi-axial MEMS mirror 227 (Microvision, Inc.) (SM) capable of two-dimensional beam deflection to large angles exceeding 500 resolvable spots, with a fast scan frequency of 20 kHz. This permits real-time confocal imaging at frame rates exceeding 30 frames per second, even at high resolution 512×512 pixel scanning. The same laser (not shown) used for Raman measurement is delivered to the probe 200 using the single mode fiber 231. A NIR laser at 825 nm is raster scanned over the sample area 290 to obtain a confocal image. The color CCD camera 240 provides information about gross lesion morphology over an area approximately 5 mm×5 mm.

The objective lens (objective assembly 228) of the imager is designed for water immersion and have an NA of at least 0.7, while a focusing mechanism 242 translates the lens element and permits imaging at the center of the field of view into the tissue to a depth of 300 μm. A hot mirror 226 (HM) in the beam path separates visible light from the beam path for use by the CCD imaging chip 240. Light for low resolution CCD imaging is provided by ring light LEDs 230 incorporated around the window of the probe 229. An aperture can be utilized to limit the NA of the CCD imaging path to allow for increased depth of focus, keeping the CCD image in focus, independent of the focus setting for the confocal images. Thus, the confocal imaging micro-probe 200 is a stand alone probe which demonstrates use for wide field color video imaging as well as in vivo confocal imaging.

Figure 3:
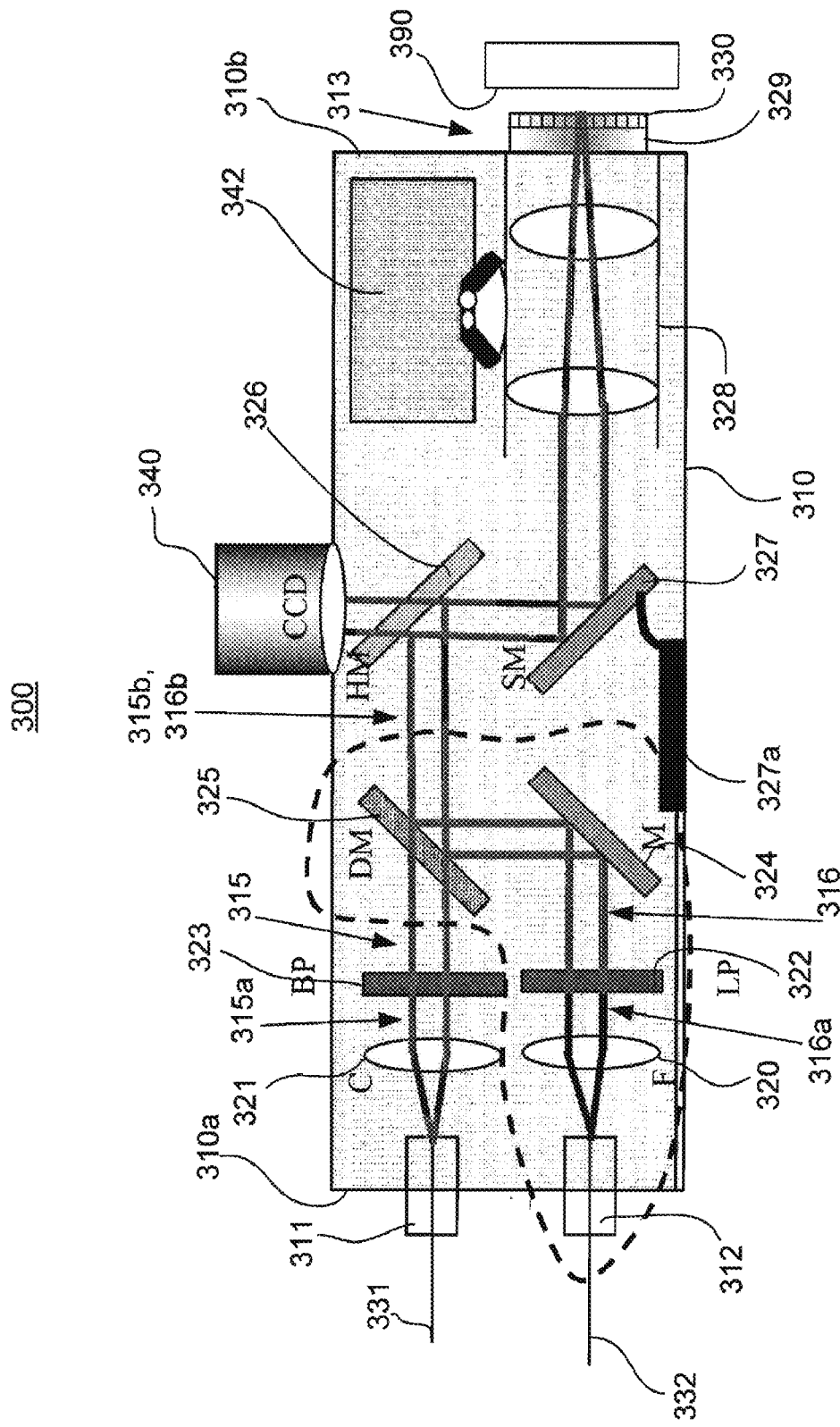
FIG. 3 shows schematically an integrated confocal Raman and confocal imaging probe for non-invasively evaluating a target of interest of a living subject, according to one embodiment of the present invention.
Figure 4:
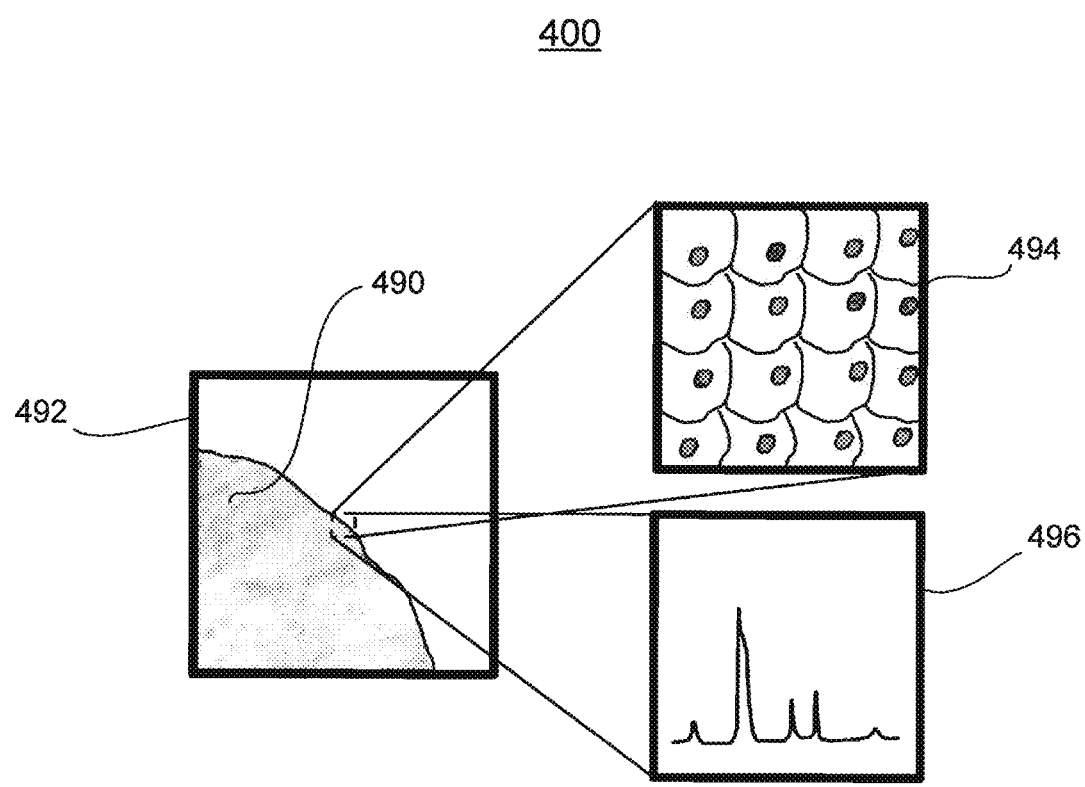
FIG. 4 shows schematically an image of a selected area of a target of interest of a living subject, and a confocal image and Raman spectrum corresponding to a specific portion within the selected area of the target of interest, captured using the probe of FIG. 3.

Now referring to FIG. 3, an integrated handheld confocal Raman/scanning confocal imaging handheld device 300 is described, in accordance with one exemplary embodiment of the present invention. The same laser as used in the configurations shown in FIGS. 1 and 2 is used at a single location, to obtain a confocal Raman spectrum, and it is raster scanned using the MEMs scan mirror 327 for confocal imaging. The optical traces of the excitation leg are co-aligned, while the detection leg separates the elastic scatter and Raman light using a dichroic mirror 325 (DM), thus allowing co-registered measurement of a cross section of skin with confocal imaging and the corresponding Raman spectrum from the center of the same area. The window of the probe 329 incorporates cross hairs marking the center of the field of view. The location of the scan mirror 329 is co-aligned with these cross-hairs. The use of a reticule will additionally assist in preventing the skin of the target of interest 390 from moving between the two measurements.

In operation, laser excitation from a laser (not shown) is delivered to the probe 300 using single mode fiber 331. The dichroic mirror 325 passes the light at 825 nm which is then directed by the scan mirror 327 onto the sample (target of interest 390 of a living subject). In the detection leg, the dichroic mirror 325 separates the backscattered Raman light from the de-scanned reflected beam and couples that Raman light into a 100 μm multimode fiber 332, which is connected to a Raman spectrometer consisting of a spectrograph and a back-illuminated, deep depletion TE-CCD camera. The objective lens of the imager (objective assembly 328) is water immersible and has an NA of at least 0.7, while a focusing mechanism 342 translates the lens element and permits imaging into the tissue (of 390) to a depth of 300 μm. The hot mirror 326 (HM) in the beam path separates visible light from the beam path for use by the CCD imaging chip 340. An aperture is used to limit the NA of the CCD imaging path, to allow for increased depth of focus, keeping the CCD image in focus independent of the focus setting for the Raman spectrum and confocal images. The use of the reticule affixed to the skin facilitates the co-registration of the bright-field image, confocal image and the Raman measurement site. Now referring to FIG. 4, in this combined probe, the low resolution CCD camera 340 captures a 5×5 mm bright-field image 492 from the investigated site. A 200×200 μm area 494 is then imaged at the center of the bright-field image 492 and at the center of that square, a Raman spectrum 496 is acquired.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] R. Richards-Kortum and E. Sevick-Muraca, "Quantitative optical spectroscopy for tissue diagnosis," *Annu Rev Phys Chem*, vol. 47, pp. 555-606, 1996.

[2] N. Ramanujam, "Fluorescence spectroscopy of neoplastic and non-neoplastic tissues," *Neoplasia*, vol. 2, pp. 89-117, 2000. "Cancer Facts and Figures," American Cancer Society, http://www.cancer.org/2004.

[3] A. Mahadevan-Jansen and R. Richards-Kortum, "Raman Spectroscopy for the Detection of Cancers and Precancers," *J Biomed Optics*, vol. 1, pp. 31-70, 1996.

[4] A. Viehoever Robichaux, D. Anderson, E. D. Jansen, A. Mahadevan-Jansen, "Organotypic raft cultures as an effective in vitro tool for understanding Raman spectral analysis of tissue", *Photochemistry and Photobiology*, 78(5), p. 517-524, 2003.

What is claimed is:

1. A probe using integrated confocal reflectance imaging, confocal Raman spectroscopy, and gross spatial imaging for non-invasively evaluating a target of interest of a living subject, comprising:
    (a) a casing with a first end and an opposite, second end;
    (b) a first optical port, a second optical port, and a third optical port, wherein the first and second optical ports are located at the first end of the casing and the third optical port is located at the second end of the casing such that the first and third optical ports define a first optical path therebetween, and the second and third optical ports define a second optical path therebetween, respectively, wherein each of the first and second optical paths has a first portion and a second portion, and wherein the second portions of the first and second optical paths are substantially overlapped and proximal to the third optical port;
    (c) a collimation lens, a coupling lens, and an objective lens assembly;
    (d) a first mirror, a second mirror, and a third mirror;
    (e) a band pass filter;
    (f) a long pass filter;
    (g) a scanning member;
    (h) an electronic imaging device; and
    (i) a focus control device,
    wherein the collimation lens, the band pass filter, and the second mirror are placed at the first portion of the first optical path, the coupling lens, the long pass filter and the first mirror are placed at the first portion of the second optical path, and wherein the third mirrors, the scanning member, and the objective assembly are placed at the overlapped second portion of the first and second optical paths.

2. The probe of claim 1, wherein in operation, excitation light is received from the first optical port and collimated by the collimation lens, passed through the band pass filter and reflected to the scanning member by the second mirror, the scanning member scans the excitation light through the objective assembly and the third optical port onto the target of interest, which in response, produces backscattered light, comprising elastically scattered light and wavelength shifted Raman light, which is collected through the third optical port by the objective assembly and de-scanned and reflected by the scanning member and the third mirror to the second mirror, from which the elastically scattered light is reflected by the second mirror to the band pass filter, and transmitted through the band pass filter and the coupling lens to the first optical port, while the wavelength shifted Raman light is reflected by the second mirror to the first mirror, and reflected by the first mirror to the long pass filter and transmitted through the long pass filter and the coupling lens to the second optical port.

3. The probe of claim 2, wherein the elastically scattered light comprises morphologic information on the target of interest.

4. The probe of claim 2, wherein the wavelength shifted Raman light comprises information on biochemical content of the target of interest.

5. The probe of claim 1, wherein the target of interest of a living subject comprises tissue of a living subject.

6. The probe of claim 1, wherein the excitation light received from the first optical port has a wavelength in the range of 600-1000 nanometers.

7. The probe of claim 1, wherein the collimating lens is adapted for collimating the excitation light received from a single mode fiber optically coupled with the first optical port.

8. The probe of claim 1, wherein the coupling lens is adapted for focusing the wavelength shifted Raman light onto a multimode fiber optically coupled with the second optical port.

9. The probe of claim 1, wherein the objective lens assembly is dynamically engaged with a focusing mechanism for selectively translating the position of the objective lens assembly in relation to the target of interest, for controlling depth of focus on the target of interest.

10. The probe of claim 1, wherein the second mirror is a dichroic mirror configured to selectively transmit the wavelength shifted Raman light and reflect away light that is not the wavelength shifted Raman light.

11. The probe of claim 1, wherein the third mirror is a hot mirror adapted for selectively transmitting the visible light for use by the electronic imaging device and reflecting away non-visible light.

12. The probe of claim 1, wherein the scanning member is a bi-axial MEMS mirror adapted for raster-scanning a beam of the excitation light onto the target of interest.

13. The probe of claim 1, wherein the electronic imaging device is a CCD camera optically coupled to the third mirror and the scanning member and adapted for receiving the visible light transmitted by the hot mirror and capturing at least one real-time image of a selected area of the target of interest from the received visible light.

14. The probe of claim 13, wherein the captured at least one real-time image is a low resolution bright-field image containing gross spatial information on the morphology of the selected area of the target of interest.

15. The probe of claim 1, further comprising an optically transparent window placed at the second end of the casing between the third port and a position where the target of interest is to be placed in operation, and having a ring LED adapted for providing bright-field illumination to the target of interest.

16. The probe of claim 1, wherein the casing of the probe is configured to be a handheld device.

17. A method of non-invasively evaluating a target of interest of a living subject, comprising the steps of:
(a) capturing at least one gross spatial image of a selected area of the target of interest;
(b) based on the at least one captured gross spatial image, selectively capturing at least one confocal image corresponding to a first specific area within the selected area of the target of interest;
(c) based on the at least one captured confocal image, selectively capturing Raman spectra corresponding to a second specific area within the first specific area of the target of interest; and
(d) comparing the captured at least one confocal image and captured Raman spectra corresponding to the target of interest with known corresponding signatures for at least one known condition for a target area of interest.

18. The method of claim 17, wherein the at least one gross spatial image is a real-time bright-field image, the at least one confocal image contains information on the morphology of the first specific area, and the Raman spectra contain information on the biochemistry corresponding to the second specific area.

19. The method of claim 17, wherein the target of interest of the living subject is skin tissue and the at least one known condition is a skin disease.

20. The method of claim 19, wherein the skin disease is a skin cancer.

21. The method of claim 20, wherein at least the steps (a)-(c) are performed with a handheld integrated probe.

22. A means for non-invasively evaluating a target of interest of a living subject, comprising:
(a) means for capturing at least one gross spatial image of a selected area of the target of interest;
(b) means for selectively capturing at least one confocal image corresponding to a first specific area within the selected area of the target of interest, based on the at least one captured gross spatial image;
(c) means for selectively capturing Raman spectra corresponding to a second specific area within the first specific area of the target of interest, based on the at least one captured confocal image; and
(d) means for comparing the captured at least one confocal image and captured Raman spectra corresponding to the target of interest with known corresponding signatures for at least one known condition for a target area of interest.

23. A method for diagnosing skin cancer, comprising the steps of:
(a) providing a handheld integrated probe for confocal reflectance imaging, confocal Raman spectroscopy, and gross spatial imaging;
(b) using the handheld integrated probe, performing the steps of:
(1) capturing at least one gross spatial image of a selected area of the skin containing a lesion of interest;
(2) based on the at least one captured gross spatial image, selectively capturing at least one confocal image corresponding to a first specific area of the lesion of interest, within the selected area of the skin; and
(3) based on the at least one captured confocal image, selectively capturing Raman spectra corresponding to a specific site of interest within the first specific area of the lesion of interest; and
(c) comparing the captured at least one confocal image and captured Raman spectra corresponding to the selected area of skin, with known corresponding signatures for normal skin tissue and malignant skin tissue.

24. An optical probe for non-invasively evaluating a target of interest of a living subject, comprising:
(a) a casing with a first end and an opposite, second end;
(b) a first optical port, a second optical port, and a third optical port, wherein the first and second optical ports are located at the first end of the casing and the third optical port is located at the second end of the casing such that the first and third optical ports define a first optical path therebetween and the second and third optical ports define a second optical path therebetween, respectively, wherein each of the first and second optical paths has a first portion and a second portion, and wherein the second portions of the first and second optical paths are substantially overlapped and proximal to the third optical port;
(c) a collimation lens, a coupling lens, and an objective lens assembly;
(d) a first mirror, a second mirror, and a third mirror;
(e) a band pass filter;
(f) a long pass filter;
(g) a scanning member;
(h) an electronic imaging device; and
(i) a focus control device,
wherein the collimation lens, the band pass filter, and the second mirror are placed at the first portion of the first optical path, the coupling lens, the long pass filter, and the first mirror are placed at the first portion of the second optical path, and wherein the third mirrors, the scanning member, and the objective assembly are placed at the overlapped second portion of the first and second optical paths.

25. The probe of claim 22, wherein the casing of the probe is configured to be a handheld device.

* * * * *